United States Patent [19]

Hattori et al.

[11] Patent Number: 5,378,623

[45] Date of Patent: Jan. 3, 1995

[54] PHOSPHOLIPASE A1, PROCESS FOR ITS PREPARATION AND THE USE THEREOF

[75] Inventors: Atsushi Hattori; Noriyoshi Uchida; Masahiro Kitaoka, all of Tokyo, Japan

[73] Assignee: Sankyo Company, Limited, Tokyo, Japan

[21] Appl. No.: 78,009

[22] Filed: Jun. 15, 1993

[30] Foreign Application Priority Data

Jun. 16, 1992 [JP] Japan ................................. 4-156264
Jan. 29, 1993 [JP] Japan ................................. 5-013508

[51] Int. Cl.$^6$ .................... C12N 9/20; C12P 13/00; C12P 9/00
[52] U.S. Cl. ................... 435/198; 435/128; 435/131
[58] Field of Search .............. 435/198, 128, 131, 134

[56] References Cited

U.S. PATENT DOCUMENTS

| | | |
|---|---|---|
| 3,652,397 | 3/1972 | Pardun . |
| 5,019,508 | 5/1991 | Johnson et al. ................ 435/198 |
| 5,153,125 | 10/1992 | Kobayashi ...................... 435/131 |

FOREIGN PATENT DOCUMENTS

| | | |
|---|---|---|
| 58-212783 | 12/1983 | Japan . |
| 62-14790 | 1/1987 | Japan . |
| 62-262998 | 11/1987 | Japan . |
| 63-42691 | 2/1988 | Japan . |
| 63-233750 | 9/1988 | Japan . |
| 3-98590 | 4/1991 | Japan . |
| 4-81431 | 12/1992 | Japan . |
| WO89/01524 | 2/1989 | WIPO . |

OTHER PUBLICATIONS

Biological Abstracts, vol. 86, Philadelphia, Pa.; Abstract No. 066261, Zhang Y et al, 'Purification and Characterization of a Lysophospholipase from a Macrophage-Like Cell Line P388D-1' of J. Biol. Chem., 263 (20) 1988, 9965–9972.
Database WPI, Section Ch, Week 8815, Derwent Publications Ltd., London, GB; Class A11, AN 88-103090 of JP-A-63 054 385 (Nippon Shoji KK) 8 Mar. 1988.
Patent Abstracts of Japan, vol. 014, No. 086 (C-0690), 19 Feb. 1990 of JP-A-01 299 292 (Q P Corp; Others: 01) 4 Dec. 1989.
Fems Microbiol. Lett., 3(2), 85–7, vol. 3, No. 2, 1978, Amsterdam NL, pp. 85–87, Blain, J. A. et al 'The nature of mycelial lipolytic enzymes in filamentous fungi'.
Biological Abstracts, vol. 72, Philadelphia, Pa., Abstract No. 012592, Chakravarti D. et al, 'Phospho Lipase Activities in Neurospora-Crassa Conidia; of Arch Biochem Biophys, 206 (2) 1981. 392–402.
Data WPI, Section Ch, Week 8815, Derwent Publications Ltd., London, GB; Class A11, AN 88-103089 of JP-A-63 054 384 (Toyo Soda Mfg KK) 8 Mar. 1988.
Biological Abstracts, vol. 64, Philadelphia, Pa., Abstract No. 004429, NIshijima M. et al, 'Detergent Resistant Phospho Lipase A of Escherichia-Coli K-12 Purification and Properties' of Eur J Biochem, 73 (1) 1977 115–124.
Contardi, et al, "Über die enzymatische Spaltung der Lecithine und Lysocithine", Biochem. Z., 261 (1933) 275.

*Primary Examiner*—Herbert J. Lilling
*Attorney, Agent, or Firm*—Frishauf, Holtz, Goodman & Woodward

[57] ABSTRACT

A Phospholipase A1 which is capable of hydrolyzing a phospholipid to produce a 2-acyl lysophospholipid and is obtainable from species of the fungus Aspergillus.

18 Claims, 7 Drawing Sheets

PHOSPHOLIPASE A1, PROCESS FOR ITS PREPARATION AND THE USE THEREOF

BACKGROUND TO THE INVENTION

The present invention relates to an enzyme capable of hydrolysing the 1-acyl group of a phospholipid, that is a Phospholipase A1, as well as to processes for the production and to the use of such an enzyme.

Phospholipases are enzymes which act on phospholipids: they are selective enzymes which are classified according to their site of action in the phospholipid molecule. Thus, a Phospholipase A1 hydrolyzes the 1-acyl group of a phospholipid, i.e. it hydrolyzes the bond between the fatty acid and the glycerine residue at the 1-position of the phospholipid. A Phospholipase A2 hydrolyzes the 2-acyl, or central acyl, group and Phospholipases C and D, which are also known as phosphodiesterases, cleave on the two sides of the phosphodiester linkage.

The hydrolysis of a phospholipid by a phospholipase results in the production of a so-called "lysophospholipid". Selective hydrolysis of a phospholipid substrate with a Phospholipase A1 produces a 2-acyl lysophospholipid and selective hydrolysis of a phospholipid with a Phospholipase A2 results in the production of a 1-acyl lysophospholipid.

Although phospholipids are used industrially, lysophospholipids have been shown to be more suitable in certain respects for industrial application. Thus, lysophospholipids show an increased solubility in water, thereby giving them enhanced emulsification properties in oil/water emulsions and an ability to form emulsions which are more stable to changing pH conditions, for example which are stable under acid conditions, and to changing temperatures. Furthermore, the ability of the lysophospholipid to form an emulsion is not reduced by the presence of ions, such as magnesium or calcium ions.

These superior properties of the lysophospholipids means that they are particularly suited for use in many industrial applications, such as in food technology, or in the cosmetics and pharmaceutical industries. It has been shown, furthermore, that the conversion of a phospholipid to a lysophospholipid in phospholipid containing substances, such as food products, generally leads to an improvement of certain of the properties of those substances. Thus, for example, a dough formed from wheat flour which contains lysophospholipids is less sticky than a dough in which the wheat flour does not contain any lysophospholipids. However, it is not yet clear whether these improvements, such as that to the dough, are attributable to the presence of the lysophospholipids alone, or to a synergistic reaction of the lysophospholipids with other substances in the product.

Lecithin is a typical phospholipid widely used in industry, for example in food technology, in animal feed products and in pharmaceutical preparations. Lecithin is a surface active agent, it has antioxidant activity and physiological activating action, as well as other properties. However, an emulsion containing lecithin is less stable than emulsions containing other surface active agents, and this is particularly demonstrated in food technology. Enzymatic hydrolysis of a phospholipid, such as lecithin, to convert at least part of it to a lysophospholipid, has been shown to improve these properties, and thus to enhance the value of the resulting lecithin derivative.

Enzymatic hydrolysis of a phospholipid, using a phospholipase isolated from a micro-organism, is known. Such hydrolysis using a Phospholipase A is described in, for example, Japanese Unexamined Patent Publication No. Sho-58-212783, and the hydrolysis using a lipase is described in Japanese Unexamined Patent Publication No. Sho-63-42691. Furthermore, the enzyme Taka-Diastase TM, which was isolated from the so-called "enzyme treasure chest" species of Aspergillus, $A.\ oryzae$ [Biochem. Z., 261 (1933) 275], has demonstrated a lipase activity which is capable of hydrolysing a phospholipid. The most commonly used phospholipase in the industrial hydrolysis of phospholipids is, however, pancreatin, an enzyme which is prepared from the pancreas of pigs and which demonstrates the activity of a Phospholipase A2.

The enzymes isolated from micro-organisms have been shown to have less activity than porcine pancreatic Phospholipase A2. Other enzymes, such as the lipases, have a lower substrate specificity as well as additional disadvantages, including a poor yield of lysophospholipid and a lower quality of lysophospholipid final product, due to the presence of by-products. Although the generic term "lipase" may appear to include phospholipases, in fact, the enzymatic activities are distinct, particularly in that the phospholipases are more selective in their site of hydrolysis than the lipases. It is furthermore apparent that some enzymes which demonstrate the activity of a phospholipase also demonstrate a separate activity which is classified as the activity of a lipase. This is more clearly demonstrated in the Examples to the present application.

Although pancreatin has better properties than those prior art enzymes isolated from micro-organisms, hydrolysis of a phospholipid using pancreatin has many disadvantages.

Firstly, it is necessary to make continual adjustments to the pH of the reaction mixture during hydrolysis of a phospholipid substrate with porcine pancreatic Phospholipase A2. The optimum pH for activity of pancreatin is in the range from neutral to weakly alkaline. During the hydrolysis reaction, however, the release of free fatty acids causes the pH to drop, that is it increases the acidity of the reaction mixture, so that, unless counter action is taken, the mixture may become acidic, and therefore outside the optimum pH for activity of the enzyme. The pH of the reaction must, therefore, be monitored carefully throughout the reaction, and it must be adjusted whenever necessary. An additional problem associated with this constant adjustment of the pH is the resulting need to remove from the final product at the end of the reaction those substances which were added to adjust the pH during the reaction.

A second problem is that pancreatin is very stable, both to heat treatment and to organic solvents, and it is therefore very difficult to de-activate the enzyme. This means that removal of residual Phospholipase A2 from the hydrolysis mixture at the end of the reaction is very difficult. The presence of residual Phospholipase A2 in the final product, in combination with any original phospholipid substrate not hydrolyzed during the reaction, leaves a potential for further reaction of the residual enzyme on the remaining substrate. The continuing activity of the phospholipase in the product results in the release of free fatty acids into the final product, resulting in a progressive change in the properties of the product. This clearly may decrease the value of the final product.

Traditionally heat treatment has been used in processes involving the use of enzymes to de-activate the residual enzyme. However, porcine pancreatic Phospholipase A2 is not sufficiently de-activated by heat treatment, and even treatment of the enzyme at a temperature of 95° C. for 30 minutes will not sufficiently de-activate the residual enzyme. The use of a higher temperature is impossible in view of the sensitivity of the phospholipid and free fatty acids to heat; these two substances are damaged or broken down at temperatures of around 120° C.

Various solutions to these two major problems have been proposed. Thus, solvent fractionation has been used to remove substances added in order to adjust the pH, as described in U.S. Pat. No. 3,652,397. Alternatively, the enzymatic reaction has been carried out in a non-ionic, non-polar organic solvent, in order to reduce the pH problem [Japanese Unexamined Patent Publication No. Hei-3-98590]. A further proposal to overcome the pH problem is described in Japanese Unexamined Patent Publication No. Sho-62-14790 and in Japanese Patent Publication No. Hei-4-81431, which demand that a compound is added to the reaction which reacts with any free fatty acid in the reaction mixture to form a water insoluble metallic soap. The problem of de-activation of the residual enzyme has been addressed by a variety of methods, for example: by a combination of solvent fractionation, using a variety of solvents, and column chromatography, using silica gel, for example; or by drying the phospholipid after treatment with a Phospholipase A2, followed by fractionation using a polar solvent [Japanese Unexamined Patent Publication No. Sho-62-262998]. A further method, described in Japanese Unexamined Patent Publication No. Sho-63-233750, involves the treatment of the Phospholipase A2 in the reaction product with a protease, followed by de-activation of the protease by heat treatment.

The solutions so far proposed to solve the problems associated with the use of porcine pancreatic Phospholipase A2 are, however, time consuming, costly and intricate. They may also result in a lower yield and affect the safety of the final product.

There remains, therefore, a need for a method for the production of lysophospholipids which can be used with confidence in many commercial and industrial applications.

The present invention provides a solution to the many problems identified above by providing a novel enzyme preparation which hydrolyzes a phospholipid to produce a lysophospholipid, which enzyme preparation is not dramatically affected by pH, and which is readily de-activated at temperatures which do not have a deleterious effect on the phospholipid or fatty acids in the reaction mixture, which enzyme preparation also has other valuable properties.

SUMMARY OF THE INVENTION

Thus, the present invention provides Phospholipase A1 obtainable from species of the fungus Aspergillus.

The present invention also provides the use of Phospholipase A1 obtainable from species of the fungus Aspergillus in the preparation of a lysophospholipid from a phospholipid.

The present invention furthermore provides a process for the preparation of a Phospholipase A1 as well as a process for the preparation of a lysophospholipid from a phospholipid, which processes are described in greater detail hereinafter.

BRIEF DESCRIPTION OF THE DRAWINGS

The present invention is to be further understood with reference to the accompanying drawings, in which:

In FIG. 4, the stability of the enzyme at different pH values was measured by mixing the enzyme with different buffers. Thus, at pH 3.2–6.0, the buffer was an aqueous acetic acid/sodium acetate solution; at pH 5.5–8.5, the buffer was an aqueous potassium monophosphate/sodium diphosphate solution and at pH 8.0–12.5, the buffer was an aqueous glycine/sodium chloride - sodium hydroxide solution.

Figure 5:
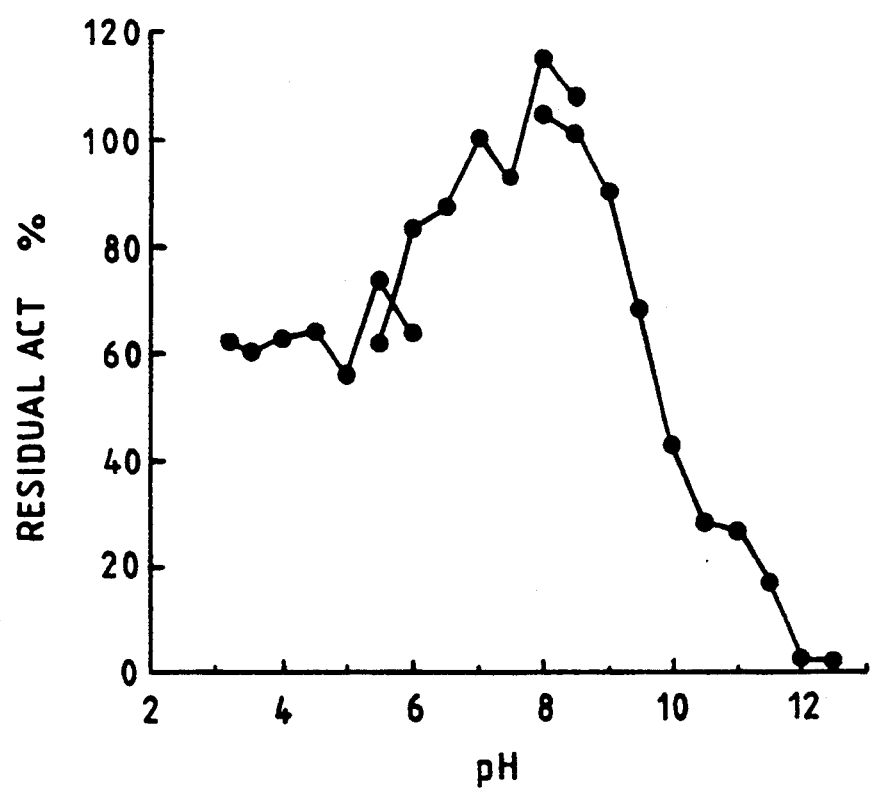
FIG. 5 shows the relationship between pH and stability of the enzyme produced according to Example 5, hereinafter.

Similarly, in FIG. 5, the stability of the enzyme at different pH values was measured by mixing the enzyme with different buffers. Thus, at pH 3.2–6.0, the buffer was an aqueous acetic acid/sodium acetate solution; at pH 5.5–8.5, the buffer was an aqueous tris aminomethane/maleic acid solution and at pH 8.0–12.5, the buffer was an aqueous glycine/sodium chloride—sodium hydroxide solution.

DETAILED DESCRIPTION OF THE INVENTION

The Phospholipase A1 of the present invention is obtainable from filamentous fungi belonging to species of the genus Aspergillus. A Phospholipase A1 is an enzyme which is capable of hydrolysing the acyl group from the 1-position of a phospholipid, an activity which is categorised under the enzyme number EC3.1.1.32 [Enzyme Nomenclature 1984, Recommendations of the Nomenclature Committee of the International Union of Biochemistry on the Nomenclature and Classification of Enzyme-Catalysed Reactions, Academic Press Inc.].

The choice of species or strain of fungus belonging to the genus Aspergillus is not essential to the present invention, so long as the micro-organism chosen produces the desired enzyme. We have found that the following micro-organisms produce the desired enzyme, and thus we generally prefer that one of these micro-organisms is used as the source for the Phospholipase A1 of the present invention.

*Aspergillus oryzae,* for example, the strain SANK 11870 or the strain available under Institute of Fermentation (IFO) number 30102;

*Aspergillus niger,* for example, the strain available under American Type Culture Collection (ATCC) number 9642 or the strain available under Institute of Fermentation (IFO) number 4407;

*Aspergillus usamii* mut. shiro usamii, for example, the strain available under Institute of Applied Microbiology (IAM) number 2414 or the strain available under Institute of Fermentation (IFO) number 6082;

*Aspergillus awamori,* for example, the strain available under Institute of Applied Microbiology (IAM) number 2112 or the strain available under Institute of Fermentation (IFO) number 4033;

*Aspergillus fumigatus,* for example, the strain available under Institute of Applied Microbiology (IAM) number 2034;

*Aspergillus sojae,* for example, the strain available under Institute of Applied Microbiology (IAM) number 2666;

*Aspergillus phoenicis,* for example, the strain available under Institute of Applied Microbiology (IAM) number 2215; and

*Aspergillus wentii,* for example, the strain available under Institute of Applied Microbiology (IAM) number 2133.

It is envisaged that not only the original natural strain but also variant strains, either naturally or artificially created, will be capable of producing the desired enzyme, and such strains are also embraced by the present invention.

We particularly prefer that either *Aspergillus oryzae* or *Aspergillus niger* is used as the source micro-organism for the Phospholipase A1 of the present invention, and we most prefer that *A. oryzae* SANK 11870 and the *A. niger* strain available under ATCC number 9642 are used as the source micro-organisms for the enzyme of the present invention.

The micro-organisms identified above are all known and have been described in the literature, for example, in Japanese Patent Publication No. Sho-46-32792; J. Gen. Appl. Microbiol., 17 (1971) 281 and Biochem. Z., 261 (1933) 275, all of which are incorporated herein by reference. Each of the micro-organisms is freely obtainable from the American Type Culture Collection in the United States of America, of from the Institute of Fermentation in Osaka, Japan, of from the Institute of Applied Microbiology in Japan, using the IAM, IFO or ATCC identification numbers provided above.

In addition, *Aspergillus oryzae* SANK 11870 has been deposited at the National Institute of Bioscience and Human Technology, of the Agency of Industrial Science and Technology, on 18th May 1993, under the conditions of the Budapest Treaty, and received the deposit number FERM BP-3887.

The Phospholipase A1 of the present invention generally has a molecular weight of between about 30,000 and 40,000 daltons, preferably between about 32,000 and 37,000 daltons, as determined by polyacrylamide gel electrophoresis in the presence of sodium dodecyl sulfate [Weber et al., J. Biol. Chem., 244 (1969) 4406]. The molecular weight of the enzyme may vary depending on the source of the enzyme, that is the enzyme when isolated from one species of Aspergillus may have a different molecular weight from the enzyme when isolated from a different species of the genus Aspergillus.

The enzymes of the present invention, that is the Phospholipase A1 which may be obtained from different species or strains of the genus Aspergillus, can also be characterised by the pH to which they migrate during isoelectric point electrophoresis (pI). We have found that the enzymes of the present invention generally have an approximate pI at pH 2.8 to 4.5, preferably pH 3.0 to 4.3, when using isoelectric point electrophoresis under standard conditions.

The Phospholipase A1 obtainable from fungi of the genus Aspergillus is superior to the prior art phospholipases, particularly in that it is an acidic phospholipase, that is it is active at a low pH. Thus, we have found that the Phospholipase A1 of the present invention demonstrates satisfactory activity in the hydrolysis of a phospholipid to produce a lysophospholipid between pH 2.5 and pH 6.0, preferably pH 3.2 to pH 5.5. The optimum pH for activity of the enzyme is dependent on certain conditions, such as the system used for the measurement of that optimum activity and the purity of the enzyme. Substances which solubilize the free fatty acid generated during the hydrolysis of the phospholipid, such as the non-ionic detergent Triton X 100 ™ (an alkyl aryl polyether alcohol) may affect the optimum pH for activity of the enzyme.

Figure 2:
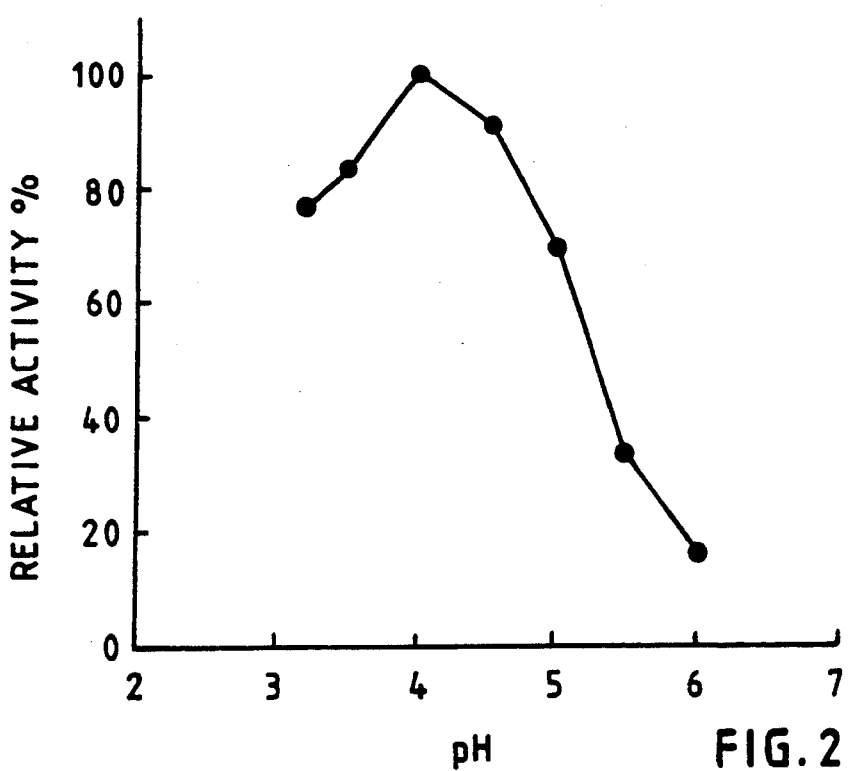
FIG. 2 shows the relationship between pH and activity of the enzyme produced according to Example 2, hereinafter, and demonstrates the optimum pH for activity of that enzyme.
Figure 7:
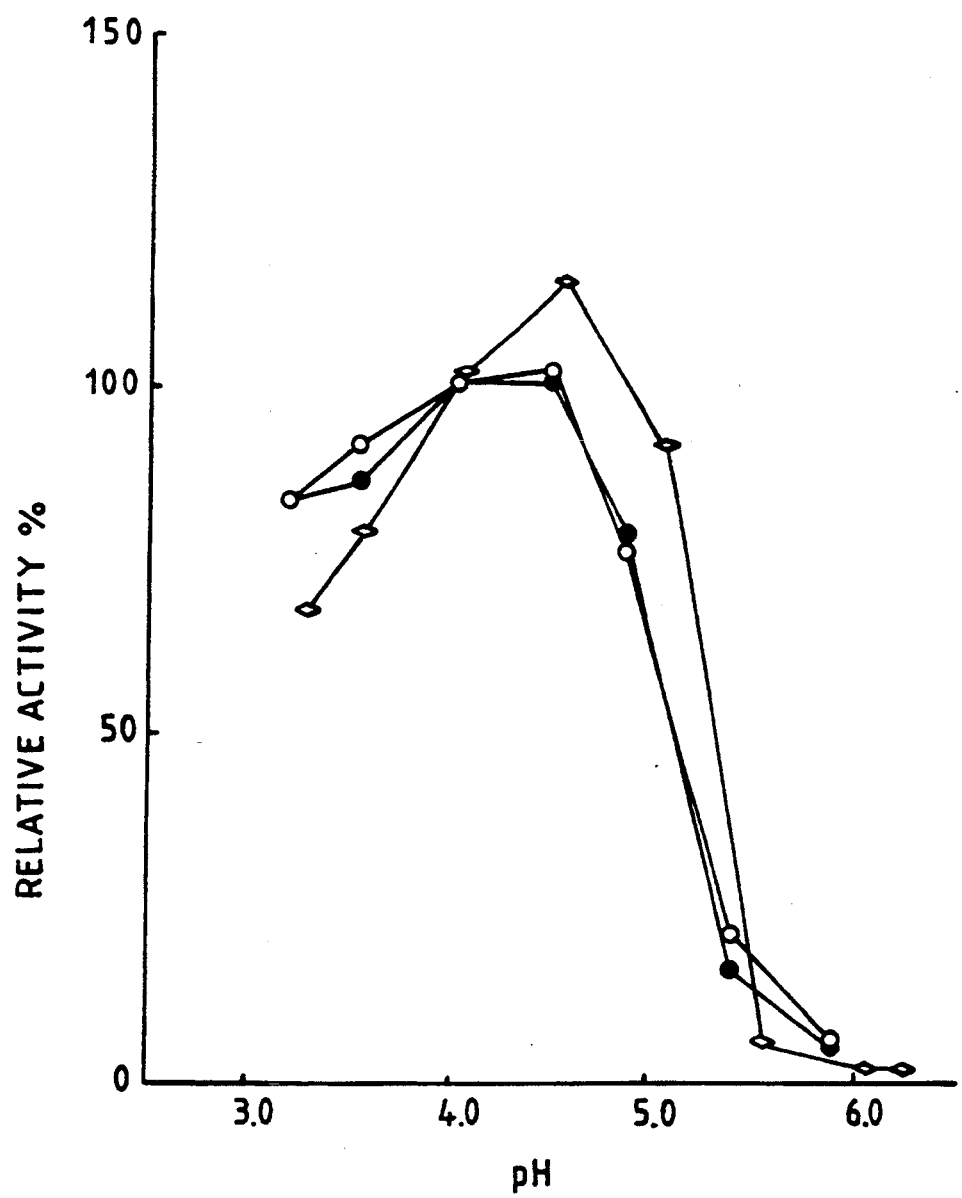
FIG. 7 shows the relationship between pH and activity of the enzyme produced according to Example 3(ii) and (iii) and Example 5, hereinafter, this activity being in the presence of the non-ionic detergent Triton X-100 TM. In this drawing, the solid circle represents the enzyme produced according to Example 3(ii) hereinafter, the empty circle represents the enzyme produced according to Example 3(iii) hereinafter, and the diamond represents the enzyme produced according to Example 5, hereinafter.

Thus, when measuring the optimum pH for activity of the enzyme by performing the reaction with an enzyme solution in 50 mM aqueous acetate buffer solution, at 37° C. for 10 minutes and in the presence of the non-ionic detergent Triton X-100 ™, the maximum activity is obtained within the range pH 3.5 to 5.0. The optimum pH for activity may also vary depending on the source of the Phospholipase A1. Thus, the samples of Phospholipase A1 obtained, for example, from the species of Aspergillus described above, have an optimum pH for activity in the presence of Triton X-100 ™ of between about pH 3.5 and 5.0, preferably about pH 4.0 (see FIGS. 2 and 7, hereinafter).

Figure 8:
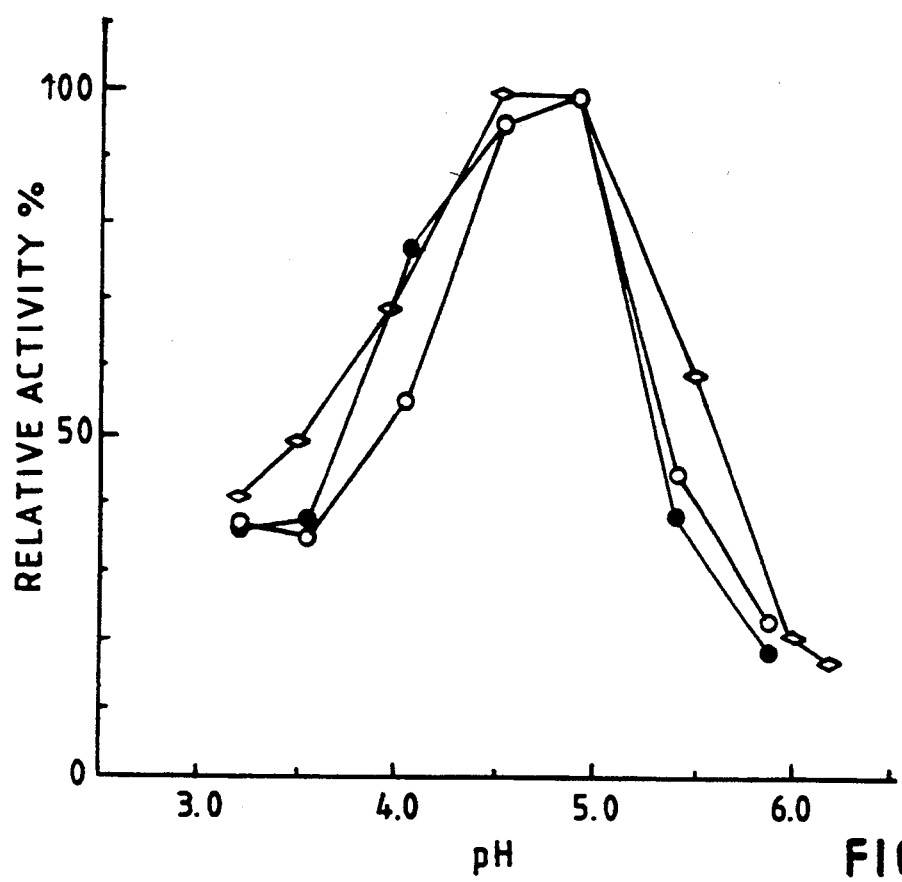
FIG. 8 shows the relationship between pH and activity of the enzyme produced according to Example 3(ii) and (iii) and Example 5, hereinafter, this activity being in the absence of the non-ionic detergent Triton X-100 TM. In this drawing, the solid circle represents the enzyme produced according to Example 3(ii) hereinafter, the empty circle represents the enzyme produced according to Example 3(iii) hereinafter, and the diamond represents the enzyme produced according to Example 5, hereinafter.

When measuring the optimum pH for activity in the absence of Triton X-100 ™, e.g. by reaction of the enzyme with the substrate in a 50 mM aqueous acetate buffer solution, at 37° C. for 10 minutes, the optimum pH for activity of the Phospholipase A1 of the present invention is within the range of about pH 4.0 to 5.5. Again, this value may differ according to the source of the phospholipase, and we have found that the Phospholipase A1 isolated from *A. oryzae* and from *A. niger* has an optimum pH for activity of about pH 4.5 to 5.5 under these conditions (see FIG. 8, hereinafter).

Figure 9:
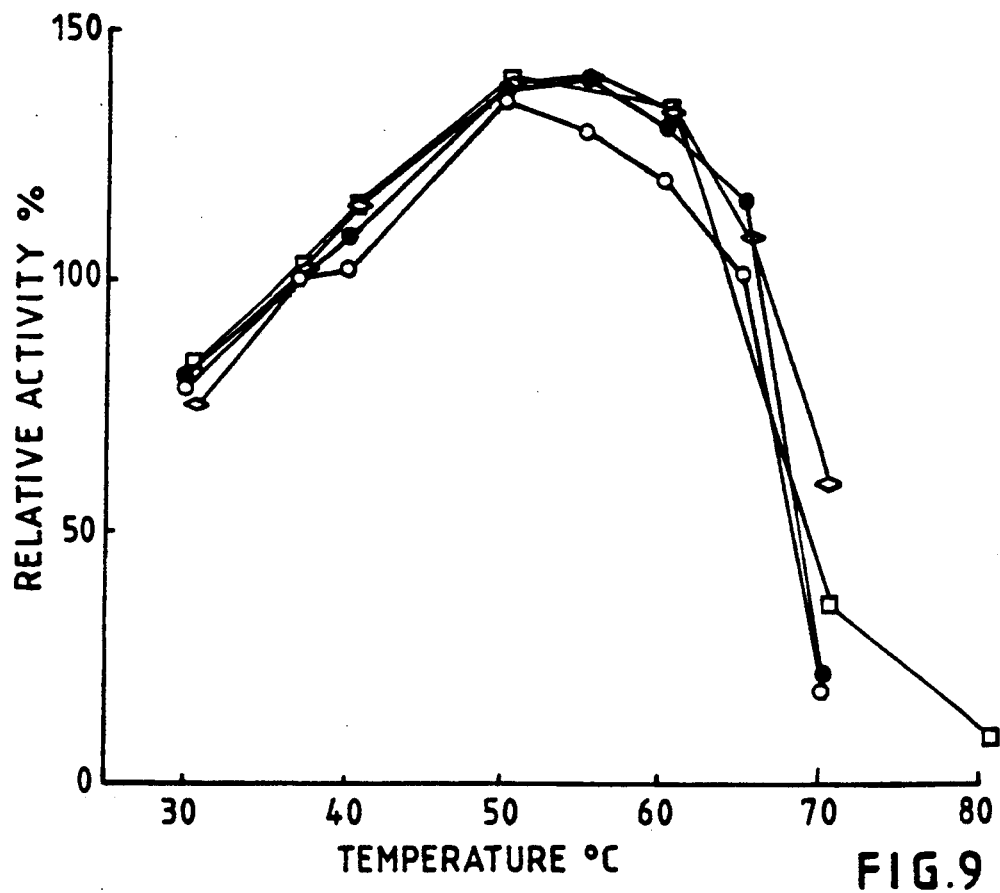
FIG. 9 shows the relationship between temperature and activity of the enzyme preparations of the present invention. In this graph, the solid circle represents the enzyme produced according to Example 3(ii) hereinafter, the empty circle represents the enzyme produced according to Example 3(iii) hereinafter, the diamond represents the enzyme produced according to Example 5 hereinafter and the square represents the enzyme produced according to Example 2 hereinafter.

Further advantages of the enzyme of the present invention are demonstrated by the range of temperatures at which the enzyme is active. We have found that the Phospholipase A1 of the present invention is active between about 30° C. and about 65° C. The temperature at which the enzyme is most active will depend on, for example, the micro-organism from which it was isolated. Thus, we have found that the enzyme isolated from *A. oryzae* is active between about 30° and 65° C., with optimum activity being demonstrated around 50°-60° C., preferably 55° C. (see FIG. 9, hereinafter). On the other hand, the Phospholipase A1 of the present invention isolated from a strain of *A. niger* demonstrates optimum activity between temperatures of about 50° and 60° C., as is shown in FIG. 9, hereinafter.

Figure 3:
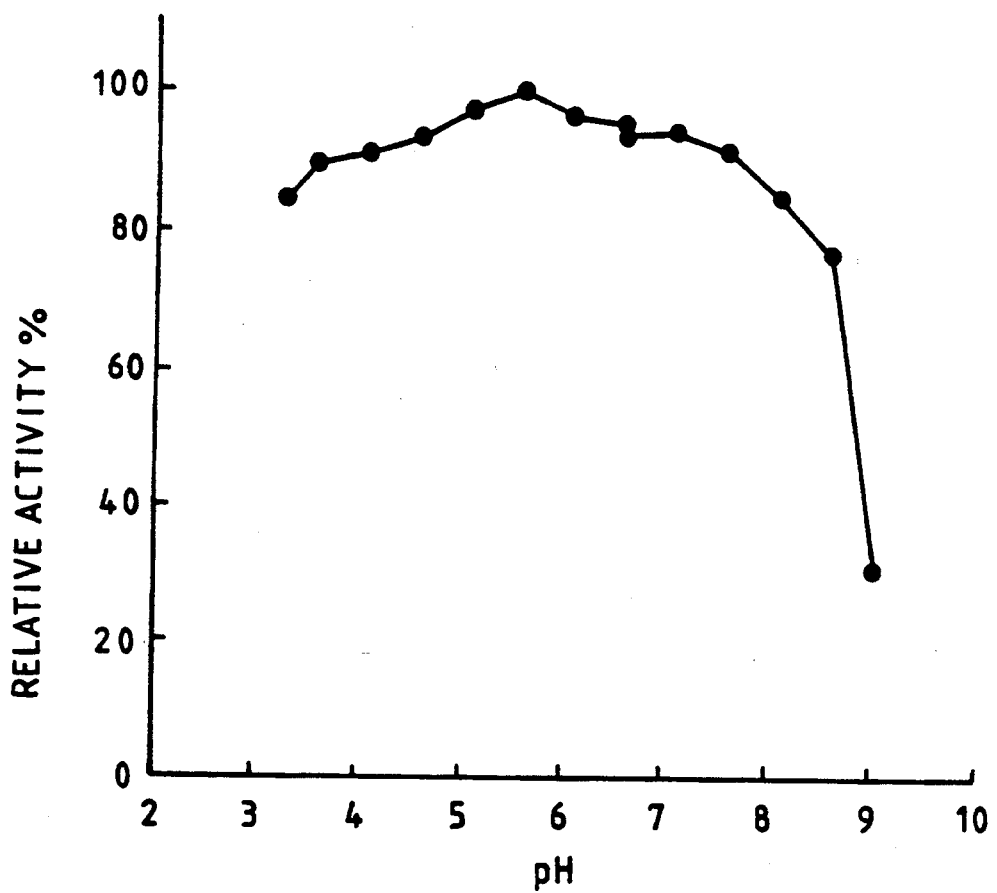
FIG. 3 shows the relationship between pH and stability of the enzyme produced according to Example 2, hereinafter.
Figure 4:
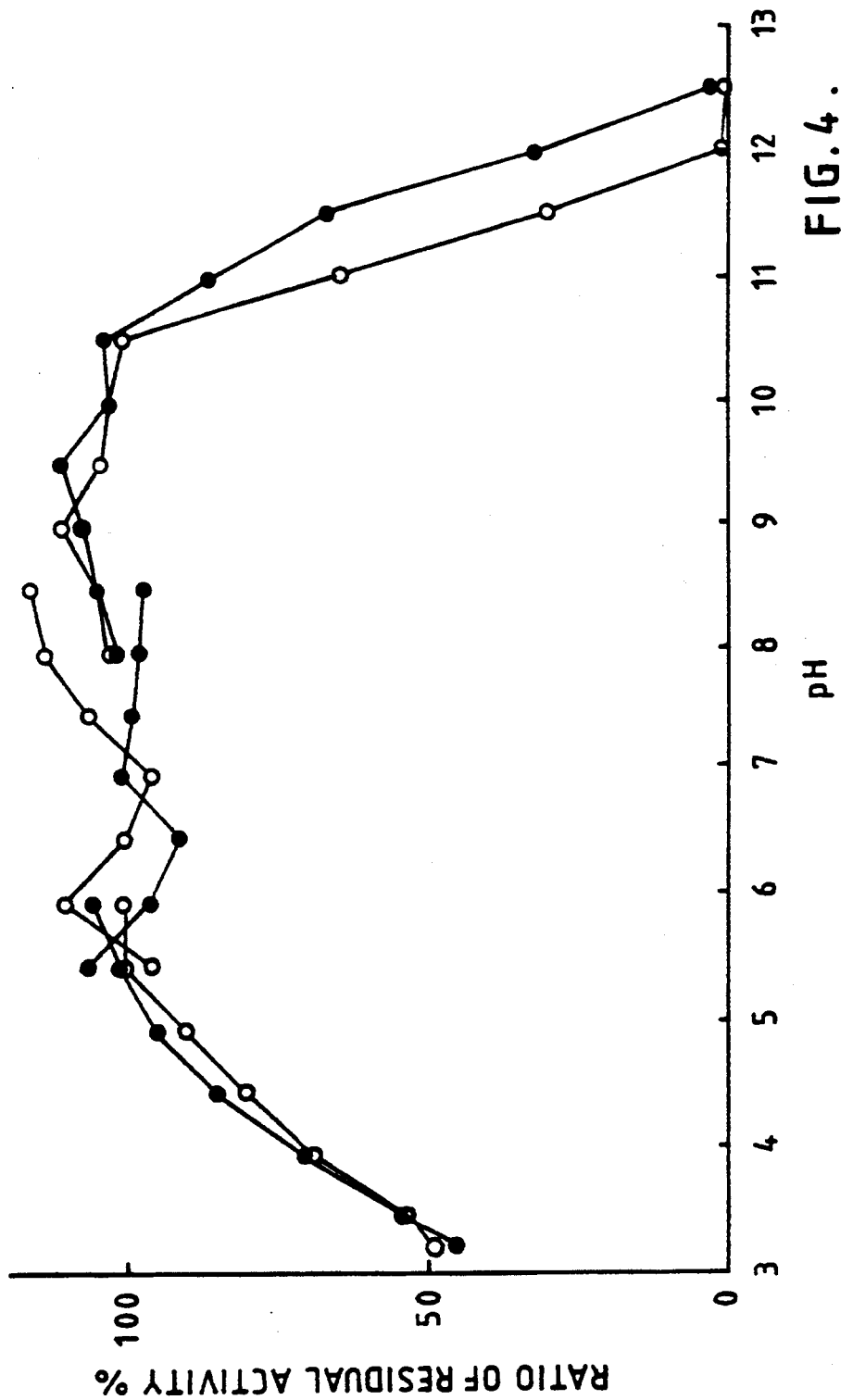
FIG. 4 shows the relationship between pH and stability of Phospholipase A1a and Phospholipase A1b, produced according to Example 3(ii) and (iii), hereinafter. The solid circle represents the Phospholipase A1a and the empty circle represents the Phospholipase A1b.

We have also found that the Phospholipase A1 of the present invention is stable across a wide, but clearly delimited, range of pH values and temperatures. The stability of the enzyme in respect of pH and temperature is, however, influenced by such factors as the concentration of the enzyme, the purity of the enzyme and the source from which the enzyme was originally isolated. In general terms, we have found that a concentration of about 10 units/ml of the Phospholipase A1 isolated from species of the fungus Aspergillus is stable at about pH 5.5 or higher, when in a 33 mM aqueous acetic acid/sodium acetate buffer solution, and at about 10.5 or less when in a 33 mM aqueous glycine/sodium chloride—sodium hydroxide buffer solution (see FIG. 4, hereinafter). Furthermore, the enzyme prepared as described in Example 2, hereinafter, has been shown to be stable between about pH 3 and about pH 8.5. These measurements were determined by measuring the Phospholipase A activity (according to the method described in Example 8(i), hereinafter) in a 1% (w/v) solution of the enzyme in either 0.2M acetate buffer (pH 3.2 to 6.5) or 0.01M tris(hydroxymethyl)aminomethane (tris) hydrochloric acid buffer (pH 6.5 to 9.0) after heat treatment at 37° C. for 60 minutes. The activity at pH 5.5 after this treatment was taken to be 100%. The results are shown in FIG. 3.

Figure 6:
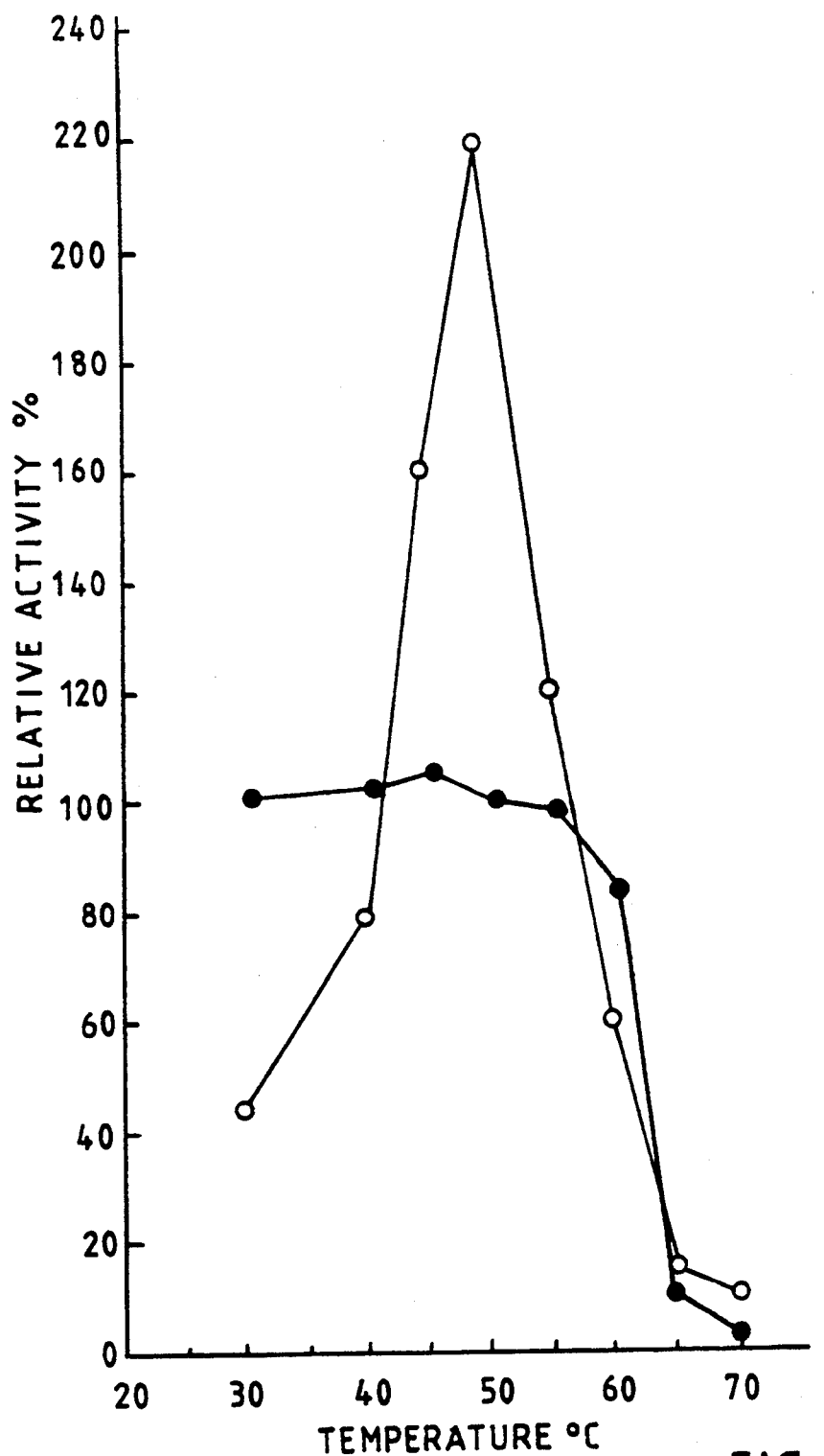
FIG. 6 shows the relationship between temperature and stability of the enzymes produced according to Examples 2 (solid circle) and 5 (empty circle), hereinafter.

The clearly delimited range of temperatures at which the Phospholipase A1 of the present invention is stable is a further advantage of the enzyme. We have found that, generally, the enzyme has an upper limit of stability to temperature within the range of from about 45° C. to about 90° C., although we prefer this upper limit to be 90° C. The temperature stability of the enzyme prepared as described in Example 2, hereinafter, is illustrated in FIG. 6. At a pH of 4.0, the enzyme is stable at temperatures of from about 30° C. to about 55° C. This value was determined by measuring the Phospholipase A activity, according to the method described in Example 8(i), hereinafter, after heat treatment of the enzyme solution at temperatures ranging between 30° and 70° C. for 30 minutes. The activity of the enzyme solution not subjected to heat treatment was taken to be 100%.

We have also observed that the enzyme preparation of the present invention does not have a crystal structure, and that the activity of the enzyme is not inhibited to any significant degree by polyvalent metal ions, such as mercury, lead and iron. Furthermore, the chelating agent, ethylenediaminetetraacetic acid (EDTA) does not have any apparent effect on the activity of the enzyme.

The preferred enzymes of the present invention are the Phospholipase A1 isolated from *A. oryzae* SANK 11870, in particular, Phospopolipase A1a and A1b having the following characteristics, and the Phospholipase A1 isolated from the strain of *A. niger* available under ATCC number 9642, having the characteristics given below.

*A. oryzae* Phospholipase A1a:
  Molecular weight:
    37,000 daltons, as determined by polyacrylamide gel electrophoresis in the presence of sodium dodecyl sulfate.
  Isoelectric point (pI):
    pI at pH 3.9, as determined by isoelectric point electrophoresis.
  Optimum active pH:
    pH 3.5 to 4.5 in the presence of Triton X-100 ™ (a non-ionic detergent) or pH 4.5 to 5.5 in the absence of Triton X-100 ™.
  Stable pH region:
    pH 5.5 or higher (with respect to an enzyme solution containing approximately 10 units/ml of enzyme in a 33 mM acetic acid/sodium acetate buffer solution) or pH 10.5 or less (with respect to an enzyme solution containing approximately 10 units/ml of enzyme in a 33 mM glycine/sodium chloride - sodium hydroxide buffer solution).
  Optimum temperature:
    50° C. to 60° C.

*A. oryzae* Phospholipase A1b:
  Molecular weight:
    35,000 daltons, as determined by polyacrylamide gel electrophoresis in the presence of sodium dodecyl sulfate.
  Isoelectric point (pI):
    pI at pH 4.3, as determined by isoelectric point electrophoresis.
  Optimum active pH:
    pH 3.5 to 4.5 in the presence of Triton X 100 ™ or pH 4.5 to 5.5 in the absence of Triton X-100 ™.
  Stable pH region:
    pH 5.5 or higher (with respect to an enzyme solution containing approximately 10 units/ml of enzyme in a 33 mM acetic acid/sodium acetate buffer solution) or pH 10.5 or less (with respect to an enzyme solution containing approximately 10 units/ml of enzyme in a 33 mM glycine/sodium chloride—sodium hydroxide buffer solution).
  Optimum temperature:
    50° C. to 60° C.

*A. niger* Phospholipase A1:
  Molecular weight:
    32,000 daltons, as measured using a Superose 12 ™ column.
  Isoelectric point (pI):

pI at pH 3.0, as determined by isoelectric point electrophoresis.

Optimum active pH:
  pH 4.0 to 5.0 in the presence of Triton X-100 TM and pH 4.5 to 5.0 in the absence of Triton X-100 TM.

Optimum temperature:
  50° C. to 60° C.

The Phospholipase A1 of the present invention is obtainable from filamentous fungi of the genus Aspergillus. The enzyme may be isolated from the desired strain of this fungus using techniques well known in the art.

More particularly, we have found that the Phospholipase A1 of the present invention can be produced by:
(a) culturing of a Phospholipase A1 producing strain of Aspergillus under conditions which allow for the production of the Phospholipase A1;
(b) at the end of the culture period, diluting the culture with water or an appropriate buffer solution;
(c) filtering the resulting solution under pressure to remove any insoluble matter; and
if desired:
(d) purifying the enzyme.

The chosen strain of Aspergillus may be cultured using the "wheat bran" culture technique. Generally, this comprises inoculating a solid or liquid grain-based medium with spores of the chosen strain, followed by culturing. The medium can be formed from any grain, such as rice, wheat, corn, soybeans, sesame seeds, or cottonseed cake, together with half to twice the weight of the grain in water. Once the water and the grain have been mixed, the resulting medium is boiled for at a suitable temperature, for example about 120° C., for a period sufficient to sterilize it, for example from 15 to 30 minutes. The medium is then cooled before use.

The inoculated medium is suitably cultured at temperatures of between 10° and 40° C., preferably between 15 and 35° C., and most preferably at between 18° and 32° C.

The length of time for which the inoculated medium is cultured depends on various factors, such as the composition of the medium and the substituents used to form the medium. However, we have generally found that, using any of the medium compositions outlined above, and culturing within the temperatures indicated above, optimum production of the enzyme is obtained after culturing for between 3 and 20 days, preferably from 4 to 8 days.

We most prefer that the inoculated medium is cultured at about 30° C. for an appropriate time, for example about 15 hours, and then that the medium is further cultured at a lower temperature, such as 19° C., for as long as desired, preferably about 5 days.

Once the culture period is over, water or an appropriate buffer solution, for example an acetate buffer or a phosphate buffer solution, is added to the cultured medium in order to dilute the medium. Suitably one to twenty times the weight of the medium in buffer or water is added to the medium. The mixture is then stirred well and the enzyme can then be removed from the solution. The enzyme may be removed from the solution using any standard technique. We have found that filtration under pressure is particularly suitable for separation of the enzyme. Typically the enzyme may be separated by straining the culture broth, diluted with an appropriate volume of water, through, for example, a layer of wire net and filter cloth in an appropriate vessel and under pressure.

The Phospholipase A1 of the present invention may be used in a state of partial purification or, alternatively, it may be purified to any desired state of purification prior to use. The state of purification may depend on, for example, the final use to which the enzyme is put. Thus, when the Phospholipase A1 of the present invention is to be added to, for example, wheat flour, for the hydrolysis of the phospholipid contained therein, it is preferred that the enzyme preparation does not contain any proteases or other similar contaminants. However, where the presence of contaminants is not of great significance in the final use of the enzyme, the enzyme can be used in a lower state of purity.

The Phospholipase A1 of the present invention, whether it is a single enzyme or is present as two distinct enzymes as produced by, for example, A. Oryzae, can be purified using techniques which are standard in the art. Such techniques include, but are not limited to, salting-out, precipitation using organic solvents, adsorption using an ion-exchanger for the adsorbent, ultrafiltration or vacuum drying. Any of these techniques can be used either alone, or in combination with another of these, or a different, technique.

The following procedure exemplifies the method for the isolation and purification of a Phospholipase A1 enzyme from a fungus of the species Aspergillus, particularly from A. oryzae SANK 11870.

After the micro-organism has been cultured for the desired length of time, cooled acetone or ethanol may be added, whilst stirring, to an extract of the cultured medium, for example a solid culture of the Aspergillus species on, for example, wheat bran. The cooled acetone or ethanol is typically added to a final concentration of about 60 to 80% (v/v). The resulting mixture is then suitably left to stand for a while, after which it is centrifuged under standard conditions, for example as illustrated in the Examples hereinafter, to obtain a precipitate. This precipitate is then suitably dissolved in an amount of a buffer solution, for example, in 50 mM acetate buffer solution (pH 5.5), after which the mixture may be salted-out using, for example, ammonium sulfate. The precipitate may then be separated by further centrifugation.

The resulting precipitate may then be dissolved in an appropriate buffer, for example, a 50 mM aqueous acetate buffer (pH 5.5) solution containing 1M ammonium sulfate. Any insoluble matter is thereby removed, allowing the residue to be purified using standard chromatographic techniques, such as column chromatography on a Butyl-Toyopearl Pak 650S TM (manufactured by Tosoh Corp.) using a 50 mM aqueous acetate buffer solution containing ammonium sulfate as the eluent.

The enzyme resulting from the first chromatography is partially purified and may, if desired, be used in that form. However, further purification steps can be taken. Such steps may include, for example, dialyzing the enzyme with a 20 mM aqueous acetate buffer solution (pH 5.5), followed by further purification using column chromatography on, for example, a Q-Sepharose TM column (manufactured by Pharmacia AB) using a 20 mM acetate buffer solution (pH 5.5) containing sodium chloride as the eluent. A Phospholipase A1 results from this purification procedure.

Further purification of the Phospholipase A1 obtained in this manner may, depending on the source micro-organism, result in the production of more than one enzyme having Phospholipase A1 activity. Thus, with the Phospholipase A1 preparation obtained in a similar manner to that described above from *A. oryzae* SANK 11870, further purification steps result in the production of Phospholipase A1a and Phospholipase A1b. Such further purification steps include, for example, salting-out with ammonium sulfate and gel filtration using a Superose 12 ™ column (manufactured by Pharmacia AB), followed by column chromatography on a MonoQ ™ column (manufactured by Pharmacia AB) using a 20 mM aqueous acetate buffer solution (pH 4.5) containing sodium chloride as the eluent.

Biological Activity

The Phospholipase A1 of the present invention is capable of hydrolysing phospholipid to produce lysophospholipid and, more specifically, it removes the 1-acyl group from the phospholipid to produce 2-acyl lysophospholipid.

In view of this, the present invention therefore also provides the use of a Phospholipase A1 obtainable from species of the fungus Aspergillus in the production of lysophospholipid from phospholipid.

The amount of the Phospholipase A1 of the present invention to be used in the hydrolysis of a phospholipid is not essential to the present invention. Furthermore, we have found that this amount may vary depending on, for example, the temperature at which the reaction is performed, the reaction time, the pH of the solution during the reaction, the properties and the quality of the particular substrate, the presence of contaminating substances, both in the enzyme preparation and in the substrate, and the amount of conversion of phospholipid to lysophospholipid desired. However, we have generally found that an amount of about 1000 units of enzyme activity per gram of substrate is sufficient. Alternatively, this can be expressed as the percentage of enzyme by weight of the substrate, for example an amount of enzyme equivalent to from 0.05% by weight to 10% by weight, preferably from 0.2% by weight to 2% by weight, of the phospholipid substrate, is sufficient.

The choice of substrate for the enzyme is virtually unlimited, so long as the substrate contains, or is phospholipid. Similarly, the concentration of the substrate is not essential to the present invention. The source and properties of the substrate phospholipid are likewise not essential to the present invention. Examples of suitable phospholipid containing substrates which may be treated with the enzyme of the present invention include: vegetable phospholipids, such as those from soybeans, wheat, barley, corn, rapeseed, safflower, sunflower, peanuts and cottonseed; phospholipids derived from animals, such as phospholipids from egg yolk, animal brain (for example, from cows, sheep, pigs and chickens) and microbially derived phospholipids, such as those from chlorella cells and filamentous fungi. The substrates which are most suitable for treatment with the enzyme of the present invention include phospholipids from soybeans, wheat or egg yolk. When using lecithin as the substrate, for example lecithin derived from wheat flour, soybeans or egg yolk, it is particularly suitable to use a concentration of lecithin of from about 1% to about 50% in the reaction mixture.

The present invention also provides a process for the hydrolysis of a phospholipid, which process comprises mixing a Phospholipase A1 obtainable from species of the fungus Aspergillus with a phospholipid containing substrate under conditions which allow hydrolysis of that substrate and, optionally, upon completion of the reaction, removing from the reaction mixture, or otherwise inactivating, residual enzyme.

In this process, it is preferred that one or both of the enzyme and the substrate is wet, and more preferably in solution, prior to mixing. The enzyme or substrate solution is suitably aqueous and appropriate solvents include ion-exchange water, distilled water, well water and tap water. When using soft water, such as ion-exchange water or distilled water, it is preferred that a small amount of a salt, such as calcium chloride, is added to the solution. The pH of the medium may be adjusted as necessary, for example to enhance the hydrolysis reaction, by the addition of an aqueous acid, such as acetic acid; an alkali, such as sodium hydroxide; or a buffer solution, such as an aqueous acetate buffer solution. The pH of the reaction mixture is suitably adjusted to a pH within the range from pH 2.5 to pH 6.5, preferably from pH 3.5 to pH 5.5.

The enzyme reaction may, if desired, be carried out in the presence of a non-ionic, non-polar organic solvent. Any suitable such solvent may be used, but we generally prefer that the solvent is an ether, such as diethyl ether or dioxane; a hydrocarbon, such as hexane, benzene or toluene; or an ester, such as ethyl acetate or butyl acetate.

The temperature at which the reaction is carried out is not essential to the present invention. Generally, however, the reaction proceeds at a satisfactory rate at temperatures of between 10° C. and 70° C., preferably from 20° C. to 65° C. We most prefer that the reaction is carried out at between 30° C. and 60° C.

The time required for the reaction varies depending on, for example, the reaction temperature and the pH. However, we have found that, under the conditions outlined above, a reaction time of between 10 minutes and 10 days, preferably between 1 hour and 2 days, results in good conversion of the phospholipid to the lyso-form.

Following the reaction, the residual enzyme may, optionally, be removed from the reaction mixture by, for example, extraction with a suitable organic solvent, or it may be otherwise treated to render it inactive, for example by heat treatment. Under normal conditions, we prefer that the residual enzyme is de-activated, although situations may arise when the need for this de-activation is not required.

We have found that the Phospholipase A1 of the present invention may be de-activated with ease by simple procedures, such as mild heat treatment, subjecting the reaction mixture to pressure, altering the pH of the reaction mixture to between about pH 3.0 and 6.0, or any combination of these techniques. Mild heat treatment is, however, the preferred method for de-activating the enzyme. In particular, we have found that heating the reaction mixture to between 45° C. and 90° C., preferably to between 50° C. and 80° C., for a period of from 5 minutes to 5 hours, preferably 10 minutes to 2 hours, will de-activate the enzyme.

When the Phospholipase A1 of the present invention is added to a substrate phospholipid for the production of a lysophospholipid, the product of the reaction may be used either with or without purification. Thus, the product of the reaction may be used directly, or it may be subjected to procedures which render it free of residual enzyme, residual substrate and any other contaminants. Examples of such procedures include filtration to remove insolubles; concentration, for example by thin layer concentration; purification using, for example, standard. chromatographic techniques; re-crystallisation, or drying, for example freeze or spray drying. Alternatively, water may be added to the lysophospholipid product, and the mixture then extracted using a water-immiscible solvent, followed by removal of the extracting solvent as necessary.

Alternatively, if desired, the Phospholipase A1 of the present invention may be added directly to a produce containing a phospholipid, for example to a wheat flour-containing dough. This may be done in order to improve the physical properties of the final product, for example bread and noodles prepared from the treated dough. Such improvements may facilitate the manipulation of the product; for example, the elasticity and spreadability of the dough may be improved, and the stickiness of the dough may be reduced. In such situations it may be desirable to add other factors at the same time, such as a Phospholipase D and an emulsifier, for example monoglyceride or calcium stearyl lactate.

The present invention is further described with reference to the following Examples, in which Examples 1 to 5 illustrate methods for the preparation of the phospholipases of the present invention and Examples 6 to 8 illustrate the application and activity of the phospholipases of the invention.

EXAMPLE 1

Preparation of Crude Phospholipase A1 from *A. oryzae*

One loopful of spores from a slant culture of *Aspergillus oryzae* (SANK 11870) were inoculated into 12 g of a medium consisting of a mixture of equal amounts by weight of wheat bran and water. The strain was then cultured at 30° C. for 6 days.

The whole of the pre-cultured strain was then inoculated into a further medium produced by placing 600 g of a mixture of equal amounts of wheat bran and water into a metal dish [42×24×7 (depth) cm] and boiling the mixture at 120° C. for 30 minutes. The strain was then cultured at 30° C. for 15 hours, after which it was cultured further at 19° C. for 5 days.

At the end of this time, 3 liters of water were added to, and thoroughly mixed into, the wheat bran mixture prepared in this way. The mixture was then allowed to stand at 37° C. for 2 hours, after which it was filtered to obtain 2.87 liters of an enzyme extract having a Phospholipase A titer of 5.9 units/ml, as determined by the method described in Example 8(i), below. Sufficient of an aqueous solution of acetic acid was then added to this enzyme extract to adjust the pH of the mixture to 4.0. An amount of cold acetone equivalent to three times the volume of the mixture was then added to the mixture, and the mixture was allowed to stand overnight in a cold room to precipitate the enzyme. The supernatant was then discarded and the precipitate was washed with acetone and dried in vacuo to obtain 11.1 g of a crude powder of Phospholipase A1, having a titer of 1,170 units/g, as determined by the method described in Example 8(i), below.

The activities of the major enzymes in this preparation, per gram of the preparation, are shown in Table 3, below.

EXAMPLE 2

Preparation of Phospholipase A1 from *A. oryzae*

10 g of crude phospholipase A1, prepared as described in Example 1, above, were dissolved in approximately 100 ml of water. Sufficient of a 1N aqueous solution of acetic acid was then added to the resulting solution to adjust the pH to 4.0. The volume of the mixture was then made up to 200 ml by the addition of water, after which 200 ml of cold acetone were added. The mixture was then allowed to stand for 1 hour. At the end of this time, the mixture was centrifuged at 5000 rpm for 10 minutes (Hitachi CR20B2 TM, Rotor: RPR 12-2) to obtain a first precipitate.

This precipitate was tested using the procedures described in Example 8(i), (ii), (iii) and (iv), hereinafter, and it was thereby determined that the precipitate had amylase activity as well as a small amount of protease activity. The precipitate also demonstrated a Phospholipase A activity of 320 units.

600 ml of cold acetone were then added to the supernatant obtained above, the resulting solution was mixed, and it was then allowed to stand for 1 hour at room temperature. At the end of this time, the mixture was centrifuged at 5000 rpm for 10 minutes (Hitachi CR20B2 TM, Rotor: RPR 12-2) to obtain a second precipitate. This second precipitate demonstrated a Phospholipase A activity of 7,800 units, when tested by the method described in Example 8(i), hereinafter.

This second precipitate was then dissolved in 500 ml of a 50 mM aqueous acetate buffer solution (pH 5.5), after which 300 g of ammonium sulfate were added to effect salting out. The precipitate was then separated by centrifuging at 10,000 rpm for 20 minutes, and the precipitate thus obtained was dissolved in about 50 ml of a 50 mM aqueous acetate buffer solution (pH 5.5) containing 1M ammonium sulfate. The insoluble matter was then filtered off, and the resulting solution was separated into its constituent parts by column chromatography using a Butyl Toyopearl Pak 650S TM column, (manufactured by Tosoh Corp.) by a gradient elution method, using a 50 mM aqueous acetate buffer (pH 5.5) solution containing ammonium sulfate at a concentration ranging between 0M and 1M as the eluent. The fraction containing a preparation having Phospholipase A1 activity, but having substantially no amylase or protease activity, eluted at an ammonium sulfate concentration of 0.6M or less. This fraction was then subjected to one of two steps:

(a) the fraction was desalted by dialysis of the fraction against water and by evaporation under reduced pressure to obtain 40 mg of Phospholipase A1; or (b) the fraction was dialyzed with a 20 mM aqueous solution of acetate buffer (pH 5.5) and then purified using column chromatography on a Q-Sepharose TM column (manufactured by Pharmacia AB), with a gradient elution method, using a 20 mM aqueous acetate buffer solution containing sodium chloride at a concentration ranging between 0 and 0.5M as the eluent. The Phospholipase A1 fraction thus obtained had 4,000 units of Phospholipase A1 activity, as determined by the method described in Example 8(i) hereinafter.

We confirmed that the enzyme preparation produced according to step (a), above, was essentially free of lipase activity, see Table 3 hereinafter, which indicates that the Phospholipase A1 produced by the method described above has a lipase activity equivalent to approximately 0.1% or less of its Phospholipase A1 activity.

We then confirmed, by the following method, that the enzyme obtained by each of the procedures described above was a Phospholipase A1. 0.0236 units of the enzyme obtained by either of step (a) or step (b), above, was reacted for 10 minutes with (i) 0.1 μmole of L-α-dipalmitoylphosphatidylcholine (1 mCi/mmole) in which the palmitoyl group at the 2-position is labelled with $^{14}$C (NEN Corp., NEC 764), and (ii) with 0.1 μmole of L-α-dipalmitoylphosphatidylcholine (2 mCi/mmole) in which the palmitoyl groups at the 1- and 2- positions are labelled with $^{14}$C (NEN Corp., NEC 682). The final volume of each reaction mixture was 90 μl. $^{14}$C-labelled palmitic acid was released only in the reaction of the enzyme with the L-α-dipalmitoylphosphatidylcholine in which both the 1- and 2- position palmitoyl groups were labelled with $^{14}$C. This is confirmation that the phospholipase preparation can hydrolyse lecithin and that this hydrolysis takes place at 1-acyl groups only.

EXAMPLE 3

Phospholipase A1a and A1b

3(i) Separation and Purification

Sufficient ammonium sulfate was added to the Phospholipase A1 preparation obtained as described in part (b) of Example 2 above, to effect salting-out. The resulting product was then filtered by gel filtration on a Superose 12 TM column (manufactured by Pharmacia AB) using a 20 mM aqueous acetate buffer solution (pH 4.5) as the eluent, followed by column chromatography on a MonoQ TM column (manufactured by Pharmacia AB) using a gradient elution method with a 20 mM aqueous acetate buffer solution (pH 4.5) containing a concentration of sodium chloride ranging from 0 to 0.25M as the eluent. This procedure results in the preparation of Phospholipase A1a having a Phospholipase A titer of 880 units and Phospholipase A1b having a Phospholipase A titer of 2,400 units.

EXAMPLE 4

Crude Phospholipase A

A procedure similar to that described in Example 1, above, was followed, but using one loopful from a slant culture of the strain *Aspergillus niger* ATCC 9642 in place of the *A. oryzae* strain used therein, to obtain 19.2 g of a crude phospholipase A1, having a titer, in the release of fatty acid from phospholipid, of 119 units/g, as determined using the method described in Example 8(i), below.

The various enzyme activities associated with this enzyme preparation are shown in Table 3, hereinafter.

EXAMPLE 5

5(i) Phospholipase A1

A similar procedure to that described in Examples 2 and 3(i), above, was followed, but using 10 g of the crude Phospholipase A1 preparation obtained in Example 4, above, in order to purify that preparation. Purification techniques used include fractionation and precipitation with acetone and column chromatography using a Butyl Toyopearl Pak 650S TM column; a Q-Sepharose TM column, and a Superose 12 TM column. 0.015 g of Phospholipase A1 in the form of a powder were produced, having a titer of 2,100 units/g, according to the method described in Example 8(i), below.

We then confirmed, by the following method, that the enzyme obtained by the procedure described above was a Phospholipase A1. 0.0236 units of the enzyme obtained above was reacted for 10 minutes with (i) 0.1 μmole of L-α-dipalmitoylphosphatidylcholine (1 mCi/mmole) in which the palmitoyl group at the 2-position is labelled with $^{14}$C (NEN Corp., NEC 764), and (ii) with 0.1 μmole of L-α-dipalmitoylphosphatidylcholine (2 mCi/mmole) in which the palmitoyl groups at the 1- and 2- positions are labelled with 14C (NEN Corp., NEC 682). The final volume of each reaction mixture was 90 μl. $^{14}$C-labelled palmitic acid was released only in the reaction of the enzyme with the L-α-dipalmitoylphosphatidylcholine in which both the 1- and 2- position palmitoyl groups were labelled with $^{14}$C. This is confirmation that the phospholipase preparation can hydrolyse lecithin and that this hydrolysis takes place at 1-acyl groups only.

The various enzyme activities associated with this enzyme preparation are shown in Table 3, hereinafter.

EXAMPLE 6

Preparation of Lysophospholipid

Various test systems were set up in order to determine the activity of the enzyme preparation of the present invention in the hydrolysis of phospholipid, as well as to determine the reliance of that reaction on pH. The various reaction systems had the following compositions: Experiment 1-A: a 10% (w/w) suspension of 5 g of SLP-White in 45 ml of water;

Experiment 2-A: a 10% (w/w) suspension of 5 g of SLP-White in 45 ml of a 20 mM aqueous solution of acetate buffer (pH 3.5);

Experiment 1-B: a 10% (w/w) suspension of 5 g of SLP-White in 45 ml of water;

Experiment 2-B: a 10% (w/w) suspension of 5 g of SLP-White in 45 ml of a 20 mM aqueous solution of tris(hydroxymethyl)aminomethane hydrochloric acid (tris-hydrochloric acid) (pH 9.0); and Experiment 3-B: a 10% (w/w) suspension of 5 g of SLP-White in 45 ml of water, with addition of sufficient of an aqueous solution of sodium hydroxide to keep the pH of the reaction mixture between 7.5 and 8.5.

[SLP-White is manufactured by True Lecithin Kogyo Co., Ltd. and it is a lecithin substrate in powder form, having a phospholipid content of not less than 95% and a phosphatidylcholine content of 23–30%.]

50 ml of each of the reaction systems listed under Experiments 1-A, 2-A, 1-B, 2-B and 3-B above, and 0.2 g of calcium chloride were placed in a 100 ml beaker, and the resulting mixture was mixed thoroughly using an ultrasonic homogenizer. After homogenization, the mixture was heated to 37° C. and the appropriate test enzymes were then added to the heated mixture, whilst stirring the mixture. Each test enzyme was used in an amount of 865 units. The beaker was then covered with a Sealon TM film (Fuji Photo Film Co. Ltd.) to prevent evaporation of moisture and the reaction mixture was stirred, whilst maintaining the temperature of the mixture at 37° C.

The test enzymes were Phospholipase A1, prepared as described in Example 2, above, and Phospholipase A2, derived from porcine pancreas (manufactured by Sigma Corp.). The activity of the Phospholipase A2 enzyme was measured at pH 8.0. phospholipase A1 was used in Experiments 1-A and 2-A above, and Phospholipase A2 was the enzyme used in Experiments 1-B, 2-B and 3-B, above.

Samples were taken from each reaction mixture at the start of the reaction, as well as at hourly intervals thereafter. Four samples were taken in all. The amount of free fatty acid in each of the samples was determined using the free fatty acid quantitative reagent, Determiner NEFA (Kyowa Medex Co., Ltd.).

The apparent phospholipid lyso conversion rate., i.e. the rate at which phospholipid was converted to lysophospholipid, was determined using the following formula:

$$A/B \times 100$$

in which:

A represents the number of moles of lysophospholipid (i.e. the number of moles of fatty acid liberated by the enzyme reaction); and B represents the number of moles of substrate phospholipid in the sample.

For this calculation it was assumed that the average molecular weight of phospholipid contained in SLP-White was 765 daltons.

The results are indicated in Table 1.

TABLE 1

| Exp. No. | Enzyme Added | Apparent Phospholipid Lyso Conversion Rate (%) [pH Value] after: | | | |
|---|---|---|---|---|---|
| | | 0 hr. | 1 hr. | 2 hrs. | 3 hrs. |
| 1-A | Phospholipase A1 | 0 [6.4] | 65 [4.7] | 86 [4.6] | 90 [4.7] |
| 2-A | Phospholipase A1 | 0 [4.8] | 79 [4.3] | 88 [4.4] | 88 [4.3] |
| 1-B | Porcine Pancreatic Phospholipase A2 | 0 [6.4] | 41 [4.3] | 48 [4.2] | 52 [4.2] |
| 2-B | Porcine Pancreatic Phospholipase A2 | 0 [7.8] | 58 [5.4] | 64 [5.2] | 71 [5.1] |
| 3-B | Porcine Pancreatic Phospholipase A2 | 0 [8.3] | 68 [7.7] | 71 [7.8] | 73 [7.7] |

As may be seen from the above results, Phospholipase A1 of the present invention demonstrated a rate of conversion of phospholipid to lysophospholipid which was superior to that of porcine pancreatic Phospholipase A2, even in the absence of a pH regulator.

Figure 1:
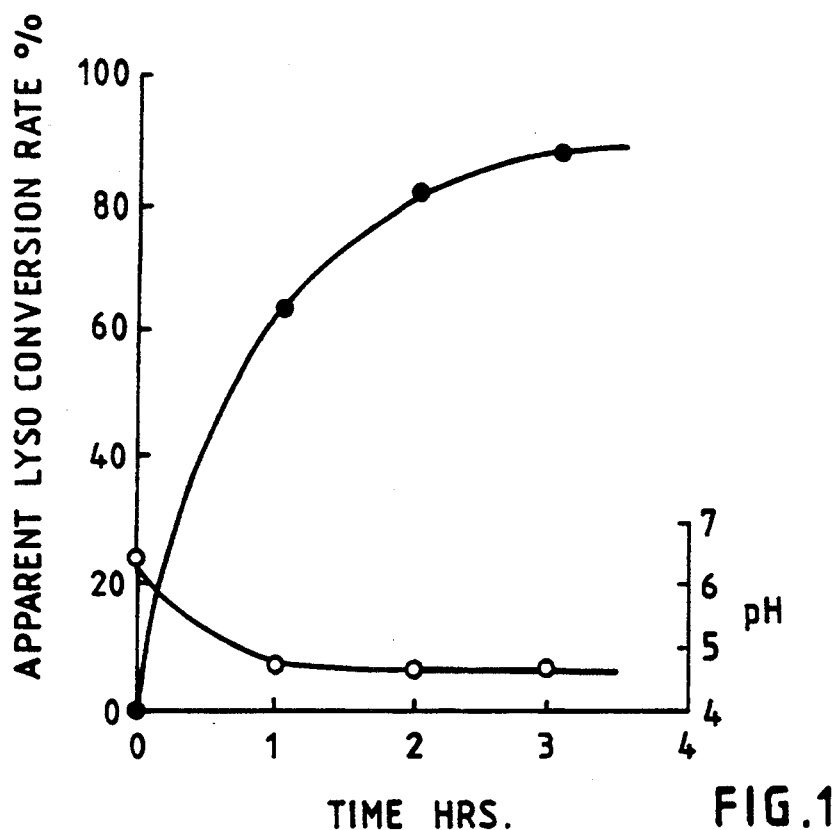
FIG. 1 represents the apparent rate of conversion of a phospholipid to a lysophospholipid, in the reaction described in Example 6, hereinafter, as well as the changes in pH of the reaction mixture during the progress of the reaction.

The apparent conversion rate of phospholipid to lysophospholipid and the changes in pH over time in Experiment 1-A are shown in FIG. 1.

EXAMPLE 7

Deactivation of Residual Enzyme by Heat Treatment

7(i) Phospholipase A1 obtained from *A. oryzae*

50 ml of a solution defined under Experiment 3-A, 4-A, 4-B or 5-B, below, and 0.2 g of calcium chloride were placed in a 100 ml beaker, and the resulting mixture was thoroughly mixed using an ultrasonic homogenizer. The mixture was then heated to a temperature of 37° C., after which test enzyme was added, whilst stirring the mixture. Each test enzyme was used in an amount of 2160 units. All of the enzyme reactions were allowed to proceed over a period of 5 hours, whilst stirring the mixtures and maintaining the mixtures at a temperature of 37° C.

The reaction systems had the following compositions:

Experiment 3-A: a 10% (w/w) suspension of 5 g of SLP-White in 45 ml of a 5 mM aqueous acetate buffer solution (pH 4.5);

Experiment 4-A: a 50% (w/w) suspension of 25 g of SLP-White in 25 ml of a 5 mM aqueous acetate buffer solution (pH 4.5);

Experiment 4-B: a 10% (w/w) suspension of 5 g of SLP-White in 45 ml of a 5 mM aqueous tris-hydrochloric acid buffer solution (pH 8.0); and Experiment 5-B: a 50% (w/w) suspension of 25 g of SLP-White in 25 ml of a 5 mM aqueous tris-hydrochloric acid buffer solution (pH 8.0).

The test enzyme used in Experiments 3-A and 4-A was Phospholipase A1 [prepared as described in Example 2] and the test enzyme used in Experiments 4-B and 5-B was porcine pancreatic phospholipase A2 (manufactured by Sigma Corp.).

The apparent rate of conversion of phospholipid to lysophospholipid at the end of the five hour period was approximately 65% in Experiment 5-B, i.e. the system in which the substrate was a 50% (w/w) suspension of SLP-White in a 5 mM aqueous tris-hydrochloric acid buffer solution, whilst the rate of conversion in the other Experiments, i.e. 3-A, 4-A and 4-B, was 90% or more.

At the end of the enzyme reaction, i.e. after the 5 hour period, approximately 7 g each of the reaction solutions were placed in several Somogyi test tubes. Each tube was covered with Sealon film, to prevent the evaporation of moisture, and the tubes were allowed to stand at temperatures of from 50° C. to 80° C. for 30 minutes. In this way, the contents of different tubes were exposed to different temperatures.

The activity of the residual Phospholipase A in each of the reaction solutions was measured according to the method described in Example 8(i), below. The residual activity of porcine pancreatic Phospholipase A2 was measured at pH 8, whilst the residual activity of the Phospholipase A1 of the present invention was measured at pH 4. The residual activity is expressed on the basis that a reaction solution not subjected to heat treatment would have a residual activity of 100%. The residual activities in the test systems are, therefore, expressed as a percentage of that un-treated reaction.

The results are indicated in Table 2.

TABLE 2

| Exp. No. | Enzyme Added | Subst. Conc. (%) | Residual Enzyme Activity (%) | | | | |
|---|---|---|---|---|---|---|---|
| | | | Un-treated | Treatment Temperature | | | |
| | | | | 50° C. | 60° C. | 70° C. | 80° C. |
| 3-A | Phospholipase A1 | 10 | 100 | 80 | 70 | 0 | 0 |
| 4-A | Phospholipase A1 | 50 | 100 | 93 | 105 | 30 | 1 |
| 4-B | Porcine Pancreatic Phospholipase A2 | 10 | 100 | 100 | 100 | 99 | 108 |
| 5-B | Porcine Pancreatic Phospholipase A2 | 50 | 100 | 102 | 102 | 101 | 100 |

The above results clearly show that the Phospholipase A1 of the present invention, which is derived from *A. oryzae*, is deactivated at a lower temperature than the Phospholipase A2 derived from porcine pancreas.

7(ii) Phospholipase A1 obtained from *A. niger*

Following a similar procedure to that described in Example 7(i), above, but using 10 ml of a 10% (w/w) suspension of 1 g of SLP-White in 9 ml of a 5 mM aqueous acetate buffer solution, 0.04 g of calcium chloride end 151 units of Phospholipase A1 (obtained from *A. niger*, as described in Example 5, above) the amount of deactivation by heat treatment of the enzyme was determined.

The apparent rate of conversion of phospholipid to lysophospholipid at the end of the five hour period of the experiment was not less than 90%.

The activity of the residual Phospholipase A1 in each of the reaction solutions was measured in accordance with the method described in Example 8(i), and this activity was expressed in the same manner as in Table 2, above.

The results are shown below.

TABLE 2A

| Exp. No. | Enzyme added | Subst. Conc. (%) | Residual Enzyme Activity | | | | |
|---|---|---|---|---|---|---|---|
| | | | Untreated | Treatment Temp. (°C.) | | | |
| | | | | 50 | 60 | 70 | 80 |
| 5-A | Phospholipase A1 | 10 | 100 | 78 | 73 | 19 | 0 |

EXAMPLE 8

The enzyme preparation of the present invention may have more than one enzyme activity associated with it. The predominant activity is that of a phospholipase, but minor amounts of lipase, amylase, acid protease and neutral and alkaline protease activities have also been demonstrated. The following are the tests used to determine these additional activities in the enzyme preparations.

8(i) Assay for Phospholipase A Activity 0.05 ml of a 0.1M aqueous solution of calcium chloride and 0.25 ml Of a 0.2M aqueous acetate buffer solution (pH 4.0) were added to 0.5 ml of a solution formed by mixing a 2.0% (w/v) suspension of SLP-White (manufactured by True Lecithin Kogyo Co., Ltd.) and 4% (v/v) Triton X-100 TM in water. Next, 0.1 ml of the appropriate enzyme solution was added to the resulting mixture, and the mixture was stirred until a homogeneous mixture resulted. The mixture obtained in this manner was left to stand at 37° C. for 10 minutes, in order to allow the enzyme reaction to take place. At the end of this time, 0.1 ml of a 1N aqueous solution of hydrochloric acid was added to the reaction mixture to stop the enzyme reaction. A sample of 0.02 ml of the reaction mixture was then taken, and this was used to determine the amount of free fatty acid. Free fatty acid was quantified using a free fatty acid quantitative reagent, Determiner NEFA (Kyowa Medex Co., Ltd.).

The enzyme activity that produces 1 μmol of fatty acid per minute of the enzyme reaction was defined as 1 unit.

8(ii) Assay for Lipase Activity 0.05 ml of a 0.1M aqueous solution of calcium chloride and 0.2M acetate buffer solution (pH 6) were added to 0.5 ml of an emulsion of 2.0% (w/v) olive oil (Wako Pure Chemical Industries, Ltd.). The olive oil emulsion was prepared by adding 10 ml of a 0.5% (w/w) aqueous solution of gum arabic to 0.2 g of olive oil, and then dispersing the mixture for 5 minutes with an ultrasonic homogenizer. 0.1 ml of the appropriate enzyme solution was then added to the mixture and the mixture was stirred until it reached homogeneity. The resulting mixture was then left to stand at 37° C. for 10 minutes, in order to allow the enzyme reaction to proceed. At the end of this time, 0.1 ml of a 1N aqueous solution of hydrochloric acid was added to the mixture in order to stop the enzyme reaction. A sample of 0.02 ml of the reaction solution was then taken, and this was used to determine the amount of free fatty acid in the mixture, using a free fatty acid quantitative reagent, Determiner NEFA (Kyowa Medex Co. Ltd.). The enzyme activity that produces 1 μmol of fatty acid per minute of the enzyme reaction was defined as 1 unit.

8(iii) Assay for Amylase (Saccharified Form) Activity 0.5 ml of substrate was placed in a test tube. The substrate was prepared by adding an appropriate amount of water, e.g. 20 ml, to 2 g of soluble starch and then heating the resulting mixture to dissolve the starch. The mixture was then cooled, 20 ml of a 0.2M aqueous acetate buffer solution (pH 4.5) were added and then water was added to bring the final volume to 50 ml.

The substrate was then heated in a thermostatic water bath kept at 37° C., and then 0.25 ml of the appropriate enzyme solution was added to the substrate. After the enzyme reaction had been allowed to proceed for 30 minutes, it was terminated by the addition of 0.25 ml of a 0.5N aqueous solution of sodium hydroxide. The amount of reduced sugar produced by the enzyme reaction was then measured in this reaction solution using the Somogyi-Nelson reduced sugar assay technique [J. Biol. Chem., 160 (1945) 61–68 and J. Biol. Chem., 153 (1944) 375–380]. The enzyme activity that produces reduced sugar equivalent to 1 μmol of glucose per minute of the enzyme reaction was defined as 1 unit.

8(iv) Assay for Protease Activity

Protease activity was measured using the method of Hagiwara [Enzyme Research Methods 2, Asakura Publishing, 237–246 (1956)]. For measurement of the three different protease activities, i.e. acid, neutral and alkaline protease, the pH of the substrate was set at different values. Thus, for the acid protease a pH of 3.0 was used and for the neutral and alkaline protease activities a pH of 7.0 was used. The enzyme activity that produces a non-protein substance demonstrating an absorbance at 275 nm which is equivalent to 1 μg of tyrosine for one minute under standard conditions in compliance with the requirements of Nothrop and Anson [Northrop, J. Gen. Physiol., 16 (1932) 41 and Anson, J. Gen. Physiol., 22 (1938) 79] was defined as one unit.

The following Table 3 shows the various enzyme activities per gram of the phospholipase preparations of the present invention.

TABLE 3

| Enzyme Type | Activity Source of Phospholipase Prep. | | | |
|---|---|---|---|---|
| | Ex. 1 | Ex. 2 | Ex. 4 | Ex. 5 |
| Phospholipase A | 1,170 | 72,100 | 119* | 2,100 |
| Lipase | ** | <100 | 56 | ** |
| Amylase | 8,740 | 3,990 | 2,468 | 17 |
| Acidic Protease | 38,800 | 50,500 | 9,140 | 280 |
| Neutral & Alkaline Protease | 230,000 | 49,000 | 6,180 | 700 |

*activity in releasing fatty acid from phospholipid, obtained from a crude enzyme preparation.
**below measurement limit (10 units)

We claim:

1. A phospholipase A1 obtained from species of the fungus Aspergillus, having the following characteristics:
   which hydrolyzes phospholipid between about pH 2.5 and about pH 6.0, having a stability to a temperature of an upper limit of between 45° and 90° C., which is stable at a temperature of less than 90° C., which has a molecular weight of between about 30,000 and 40,000 daltons, as determined by sodium dodecyl sulfate polyacrylamide gel electrophoresis, which has pI under isoelectric point electrophoresis at about pH 2.8 to about pH 4.5, which has an optimum temperature for activity of from pH 3.2 to about pH 5.5, and which has an optimum temperature for activity of from about 30° to 65° C.

2. The phospholipase A1 according to claim 1 which is stable at a pH of between about pH 3 and about pH 10.5.

3. Phospholipase A1 according to claim 1 which has a molecular weight of between about 32,000 and 37,000 daltons as determined by sodium dodecyl sulfate polyacrylamide gel electrophoresis.

4. The phospholipase A1 according to claim 1 which has a pI under isoelectric point electrophoresis at about pH 3.0 to about pH 4.3.

5. The phospholipase A1 according to claim 1 which has an optimum temperature for activity of from about 50° to 65° C.

6. Phospholipase A1 according to claim 1 which is obtainable from a fungus selected from the group consisting of:
Aspergillus oryzae;
Aspergillus niger;
Aspergillus usamii mut. Shiro usamii;
Aspergillus awamori;
Aspergillus fumigatus;
Aspergillus sojae;
Aspergillus phoenicis;
Aspergillus wentii;
Aspergillus oryzae SANK 11870 FERM BP-3887;
Aspergillus oryzae available under Institute of Fermentation number 30102;
Aspergillus niger, available under American Type Culture Collection number 9642;
Aspergillus niger, available under Institute of Fermentation number 4407;
Aspergillus usamii mut. shiro usamii, available under Institute of Applied Microbiology number 2414;
Aspergillus usamii mut. shiro usamii, available under Institute of Fermentation number 6082;
Aspergillus awamori, available under Institute of Applied Microbiology number 2112;
Aspergillus awamori, available under Institute of Fermentation number 4033;
Aspergillus fumigatus, available under Institute of Applied Microbiology number 2034;
Aspergillus sojae, available under Institute of Applied Microbiology number 2666;
Aspergillus phoenicis, available under Institute of Applied Microbiology number 2215; and
Aspergillus wentii, available under Institute of Applied Microbiology number 2133.

7. Phospholipase A1 according to claim 1 which is isolated from Aspergillus oryzae SANK 11870, available under deposit number FERM BP-3887.

8. Phospholipase A1 according to claim 1 which is isolated from the strain of Aspergillus niger obtainable under American Type Culture Collection number 9642.

9. The phospholipase according to claim 3, which has a pI under isoelectric point electrophoresis at a pH of 3.0 to 4.3.

10. The phospholipase according to claim 3, which has an optimum temperature for activity of 50° to 65° C.

11. The phospholipase according to claim 9 which has an optimum temperature for activity of 50° to 65° C.

12. The phospholipase according to claim 9, which is stable at a pH of 3 to 10.5.

13. The phospholipase according to claim 1, which hydrolyzes the acyl group of the 1-position of a phospholipid to produce a 2-acyl lysophospholipid.

14. The phospholipase according to claim 1, which has an activity which is categorized by an enzyme number of EC 3.1.32.

15. The phospholipase according to claim 1, which has a lipase activity equivalent to 0.1% or less of its phospholipase A1 activity.

16. A phospholipase A1a obtained from Aspergillus oryzae SANK 11870 FERM BP-3887 and having the following characteristics:
molecular weight:
37,000 daltons, as determined by polyacrylamide gel electrophoresis in the presence of sodium dodecyl sulfate;
isoelectric point:
a pI at pH 3.9, as determined by isoelectric point electrophoresis
optimum active pH:
a pH of 3.5 to 4.5 in the presence of an alkyl aryl polyether alcohol non-ionic detergent or a pH of 4.5 to 5.5 in the absence of said alkyl aryl polyether alcohol non-ionic detergent
stable pH region:
a pH 5.5 or higher, with respect to an enzyme solution containing approximately 10 units/ml of enzyme in a 33 mM acetic acid/sodium acetate buffer solution, or a pH of 10.5 or less, with respect to an enzyme solution containing approximately 10 units/ml of enzyme in a 33 mM glycine/sodium chloride—sodium hydroxide buffer solution; and
optimum temperature:
50° C. to 60° C.

17. A phospholipase A1b obtained from Aspergillus oryzae SANK 11870 FERM BP-3887 and having the following characteristics:
molecular weight:
35,000 daltons, as determined by polyacrylamide gel electrophoresis in the presence of sodium dodecyl sulfate;
isoelectric point:
a pI at pH 4.3, as determined by isoelectric point electrophoresis;
optimum active pH:
a pH of 3.5 to 4.5 in the presence of an alkyl aryl polyether alcohol non-ionic detergent or a pH of 4.5 to 5.5 in the absence of said alkyl aryl polyether alcohol non-ionic detergent
stable pH region:
a pH of 5.5 or higher, with respect to an enzyme solution containing approximately 10 units/ml of enzyme in a 33 mM acetic acid/sodium acetate buffer solution, or a pH of 10.5 or less, with respect to an enzyme solution containing approximately 10 units/ml of enzyme in a 33 mM glycine/sodium chloride—sodium hydroxide buffer solution; and optimum temperature:
  50° C. to 60° C.

18. A phospholipase A1 obtained from *Aspergillus niger* ATCC 9642 and having the following characteristics:

molecular weight:
  32,000 daltons, as measured using a Superose 12 ™ column;
isoelectric point:
  a pI at pH 3.0, as determined by isoelectric point electrophoresis;
optimum active pH:
  a pH of 4.0 to 5.0 in the presence of an alkyl aryl polyether alcohol non-ionic detergent and a pH of 4.5 to 5.0 in the absence of said alkyl aryl polyether alcohol non-ionic detergent; and
optimum temperature:
  50° C. to 60° C.

* * * * *